United States Patent [19]

Cassal et al.

[11] 4,064,173
[45] Dec. 20, 1977

[54] 9,10-SECO-STEROIDS

[75] Inventors: Jean-Marie Cassal, St. Louis, France; Andor Fürst, Basel; Werner Meier, Bottmingen, both of Switzerland

[73] Assignee: Hoffmann-La Roche, Inc., Nutley, N.J.

[21] Appl. No.: 651,763

[22] Filed: Jan. 23, 1976

Related U.S. Application Data

[62] Division of Ser. No. 533,101, Dec. 16, 1974, abandoned.

[30] Foreign Application Priority Data

Dec. 21, 1973 Switzerland .................. 18029/73

[51] Int. Cl.$^2$ .............................................. C07C 49/27
[52] U.S. Cl. ........................... 260/586 E; 260/293.56; 260/326.8; 260/340.5 AS; 260/340.9 AS; 260/345.2; 260/397.5; 260/464; 260/562 R; 260/347.4; 260/347.7; 260/347.8; 560/108; 560/139; 560/21
[58] Field of Search ..................... 260/586 E

[56] References Cited

U.S. PATENT DOCUMENTS 3,637,754  1/1972  Bucourt et al. ............. 260/586 E X

FOREIGN PATENT DOCUMENTS 1,419,629  12/1975  United Kingdom ............ 260/586 E Primary Examiner—Ethel G. Love
Attorney, Agent, or Firm—Samuel L. Welt; George M. Gould; Raymond R. Wittekind

[57] ABSTRACT

A process for the preparation of 9,10-seco-steroids of the formula

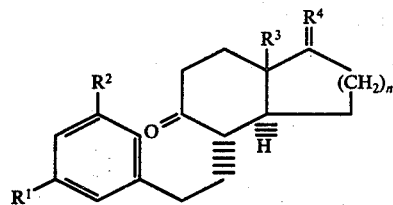

wherein $R^1$ and $R^2$ independently are hydrogen, amino, $OR^5$, $OCOR^6$ or $NHCOR^5$ wherein $R^5$ is hydrogen or lower alkyl and $R^6$ is lower alkyl or phenyl; $R^3$ is lower alkyl; $R^4$ is oxo,

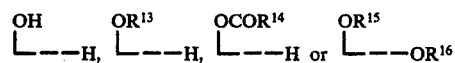

wherein $R^{13}$ is lower alkyl, lower alkoxy — lower alkylene, tetrahydropyranyl or tetrahydrofuryl, $R^{14}$ is lower alkyl or aryl and $R^{15}$ and $R^{16}$ are lower alkyl or taken together form lower alkylene or arylene, and $n$ is 1 or 2 is disclosed. The 9,10-seco-steroids of this invention are useful intermediates for the preparation of steroids.

10 Claims, No Drawings

9,10-SECO-STEROIDS

This is a division of application Ser. No. 533,101 filed Dec. 16, 1974, now abandoned.

DESCRIPTION OF THE INVENTION

The present invention relates to novel 9,10-seco-steroids and to processes for the preparation thereof. More specifically, the present invention relates to 9,10-seco-steroids represented by the general formula

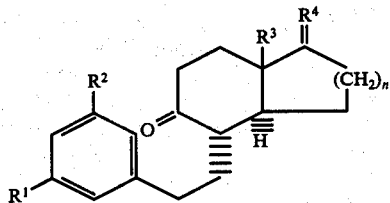

wherein $R^1$ and $R^2$ independently are hydrogen, amino, $OR^5$, $OCOR^6$ or $NHCOR^5$ wherein $R^5$ is hydrogen or lower alkyl and $R^6$ is lower alkyl or phenyl; $R^3$ is lower alkyl; $R^4$ is oxo,

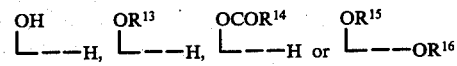

wherein $R^{13}$ is lower alkyl, lower alkoxy-lower alkylene, tetrahydropyranyl or tetrahydrofuryl, $R^{14}$ is lower alkyl or aryl and $R^{15}$ and $R^{16}$ are lower alkyl or taken together from lower alkylene or arylene, and n is 1 or 2.

As used throughout the specification and appended claims, the term "lower" denotes a group having a carbon skeleton containing up to and including 7 carbon atoms; the term "alkyl" signifies a monovalent radical derived from a saturated branched or straight chain hydrocarbon; the term "alkoxy" denotes a radical derived from an alcohol having a saturated branched or straight chain hydrocarbon residue by abstraction of the proton bound to oxygen; the term "alkylene" signifies a divalent radical derived from a saturated branched or straight chain hydrocarbon; and the term "arylene" denotes a divalent radical derived from an aromatic hydrocarbon. Examples of lower alkyl groups are methyl, ethyl, propyl, isopropyl and tert.-butyl, the preferred lower alkyl groups being methyl, ethyl and tert.-butyl. Examples of lower alkoxy-lower alkylene groups are methoxymethylene and 2-methoxy-2,2-dimethylmethylene. Examples of lower alkylene groups are ethylene, propylene and 2,2-dimethylpropylene. An example of an aryl group is phenyl and examples of arylene groups are 1,2-phenylene or 3,4-naphthylene. The configuration of the various substituents attached to the 9,10-seco-steroids of this invention represented by structural formulas throughout the specification and appended claims is signified by three notations. With respect to substituents attached to the bicyclic system, a solid line (—) denotes a substituent attached in the beta-configuration, i.e., a substituent attached in the configuration above the plane of the paper; a dotted line (---) denotes a substituent attached in the alpha-configuration i.e., a substituent attached in the configuration below the plane of the paper, and a wiggly line (⌇) denotes a substituent in either the alpha- or beta-configuration. With respect to substituents attached to the 1- or alpha-position of the phenethyl side-chain, a wiggly line (⌇) denotes a substituent attached in either one of the two possible stereochemical configurations.

The alkyl group bound to the 13-position of the 9,10-seco-steroid nucleus has been arbitrarily assigned the beta-configuration, which is consistent with the absolute stereochemistry of the products described in the examples. The formulas presented in the specification and appended claims, however, are not limiting. It is intended that these formulas represent both enantiomeric series and mixtures thereof, for example, racemic mixtures.

Preferred compounds of formula I are those wherein $R^3$ is methyl or ethyl, $R^4$ is beta-tert.butoxy or beta-methoxymethyleneoxy, $R^1$ is methoxy or amino, $R^2$ is hydrogen or methoxy, and n is 1.

The 9,10-seco-steroids of formula I are prepared by condensing a bicyclic 2-methylene ketone of formula II

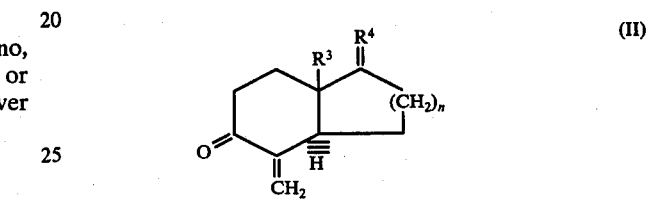

wherein $R^3$, $R^4$ and n are as hereinbefore defined, with an alpha-nitrotoluene of formula III

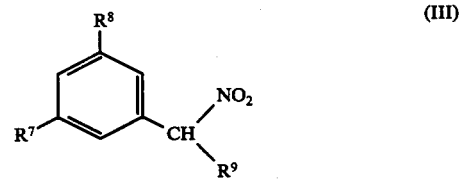

wherein $R^7$ and $R^8$ independently and respectively are $R^1$ and $R^2$, nitro, benzyloxy, diphenylmethoxy or triphenylmethoxy and $R^9$ is hydrogen, cyano or $COOR^{10}$ wherein $R^{10}$ is lower alkyl or benzyl, in the presence of a basic catalyst to give a 6-nitro-seco-steroid of formula IV

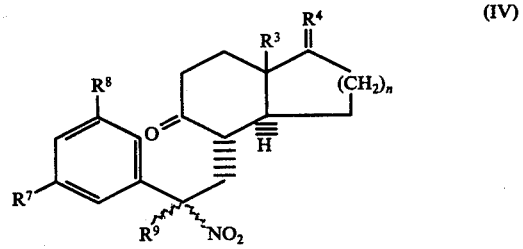

wherein $R^3$, $R^4$, $R^7$, $R^8$, $R^9$ and n are as hereinbefore defined, followed by saponification and decarboxylation of the 6-cyano or 6-alkoxycarbonyl or 6-benzyloxycarbonyl group, if present, and hydrogenolysis of the 6-nitro group in the presence of a noble metal or nickel catalyst.

The condensation of a bicyclic ketone of formula II with an alpha-nitrotoluene of formula III is performed in a suitable organic solvent, for example, a hydrocarbon such as pentane, hexane, benzene or toluene, an ether such as diethyl ether, dioxane or tetrahydrofuran, an alcohol such as methanol, ethanol or tert.-butanol or an amide such as dimethylformamide or dimethylacetamide, at room or elevated temperature, preferably at or about room temperature, in the presence of a basic catalyst. A wide variety of bases may be employed. For example, metal alcoholates such as sodium methylate or sodium ethylate, metal hydrides such as sodium hydride, tertiary amines such as triethylamine and quaternary ammonium hydroxides such as benzyltrimethylammonium hydroxide may be utilized. While the amount of base employed is not critical, catalytic amounts of base are preferred, catalytic amounts of base of 1 to 10 mol percent being particularly preferred.

In an alternate embodiment of the invention, 6-nitro-seco-steroids of formula IV are prepared by adding the preformed alkali metal salt, preferably the sodium salt, of an alpha-nitrotoluene of formula III, prepared by treating an alpha-nitrotoluene of formula III with an alkali metal alcoholate such as sodium methylate or an alkali metal hydride such as sodium hydride and a suitable solvent, for example, an alcohol such as methanol or an amide such as dimethylformamide or dimethylacetamide, to a solution of a bicyclic alpha-methylene ketone of formula II also in a suitable alcoholic solvent such as methanol or amidic solvent such as dimethylformamide or dimethylacetamide.

In another alternate embodiment of the invention, the bicyclic alpha-methylene ketone of formula II is generated in situ, i.e., the compound of formula II is formed in the reaction mixture. In this embodiment of the invention, a bicyclic ketone of formula IIa

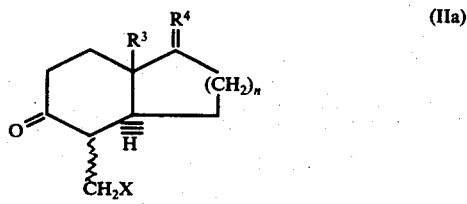

wherein $R^3$ is lower alkyl; $R^4$ is oxo,

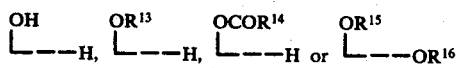

wherein $R^{13}$ is lower alkyl, lower alkoxy-lower alkylene, tetrahydropyranyl or tetrahydrofuryl, $R^{14}$ is lower alkyl or aryl and $R^{15}$ and $R^{16}$ are lower alkyl or taken together form lower alkylene or arylene; X. is $OR^{11}$, $N(R^{12})_2$, $SR^{11}$, $N^+(R^{12})_3$, $R^{12}$

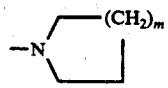

or $S(R^{12})_2$ wherein $R^{11}$ is hydrogen, lower alkyl, acetyl or benzoyl, $R^{12}$ is lower alkyl, and m is 1 or 2, is treated with an alpha-nitrotoluene of formula III under the conditions utilized for the condensation of compounds of formulas II and III in the presence of a base to give a compound of formula IV.

Cyano or ester groups attached to the 6-position of 9,10-seco-steroids of formula IV are saponified by alkali, for example sodium hydroxide, to the corresponding carboxylate salts which readily decarboxylate upon treatment with a mineral acid, such as hydrochloric acid, to 6-nitro-seco-steroids of formula IVa

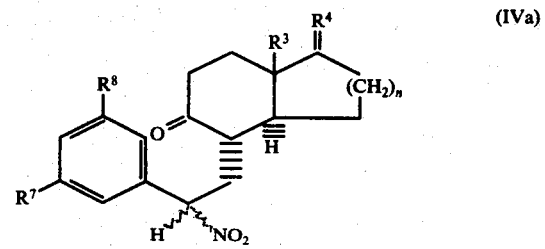

Wherein $R^3$, $R^4$, $R^7$, $R^8$ and n are as hereinbefore defined.

The conversion of 6-nitro-9,10-seco-steroids of formula IVa to 9,10-seco-steroids of formula I is effected by hydrogenation in the presence of a hydrogenation catalyst. In this embodiment of the invention, a solution of a 6-nitro-9,10-seco-steroid of formula IVa and a suitable inert organic solvent, for example, a hydrocarbon such as pentane, hexane, benzene or toluene, an ether such as diethyl ether, dioxane or tetrahydrofuran, an alcohol such as methanol, ethanol or tert.butanol or an amide such as dimethylformamide or dimethylacetamide, dimethylformamide being preferred, is hydrogenated in the presence of a noble metal or nickel catalyst. As the noble metal catalyst, palladium is preferred, palladium/carbon is especially preferred and 5 to 10% palladium carbon is particularly preferred. As the nickel catalyst, Raney nickel is preferred. During the course of the hydrogenolysis of the 6-nitro group of compounds of formula IVa, nitro groups affixed to the aromatic A-ring are reduced to amino groups and benzyloxy, diphenylmethoxy and triphenylmethoxy also attached to the aromatic A-ring are cleaved to phenols.

The aforementioned hydrogenolysis of compounds of formula IVa may be accomplished by employing solutions of compounds of formula IVa obtained directly in the condensation step of compounds of formulas II and III wherein $R^9$ of formula II is hydrogen or the saponification-decarboxylation step of compounds of formula IV wherein $R^9$ is cyano or $COOR^{10}$ wherein $R^{10}$ is lower alkyl or benzyl.

9,10-seco-steroids of formula I wherein $R^1$ and $R^2$ independently are hydrogen, amino, $OR^5$, $OCOR^6$ or $NHCOR^5$ wherein $R^5$ is hydrogen or lower alkyl and $R^6$ is lower alkyl or phenyl; $R^3$ is lower alkyl; $R^4$ is oxo,

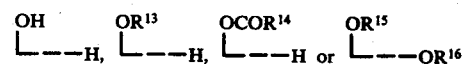

wherein $R^{13}$ is lower alkyl, lower alkoxy-lower alkylene, tetrahydropyranyl or tetrahydrofuryl, $R^{14}$ is lower alkyl or taken together form lower alkylene or arylene, and n is 1 or 2, with the proviso that $R^5$ is hydrogen when n is 1 or $R^2$ is a group other than hydrogen, are novel compounds and are included within the scope of the invention.

The 9,10-seco-steroids of this invention are useful intermediates for the preparation of steroids, especially steroids of the estrone series. As depicted in Chart A, steroids of formulas V and VI wherein $R^1$, $R^2$, $R^3$, $R^4$ and n are as hereinbefore defined, and prepared by cyclization of compounds of formula I followed by reduction of the 9,11-double bond of compounds of formula V. Specifically, compounds of formula I are cyclized to compounds of formula V in the presence of a mineral acid, for example hydrochloric acid, or an organic acid, for example p-toluenesulfonic acid, the preferred acid concentration being 0.5N to 4N, at 0° to 30°, and compounds of formula V are reduced to compounds of formula VI by hydorgen in the presence of a palladium/carbon catalyst, preferably a 5% palladium/-carbon catalyst.

Chart A

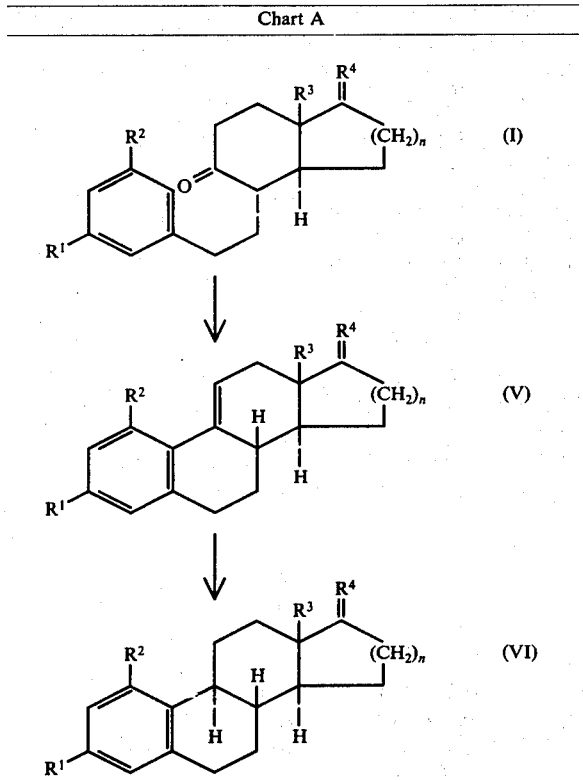

The following Examples further illustrate the present invention, which is not restricted thereto.

In the following examples, NMR denotes nuclear magnetic resonance.

EXAMPLE 1 a. 7.5 g of (+)-1β-tert.butoxy-3aα,6,7,7a-tetrahydro-7aβ-methyl-4-methylene-indan-5(4H)-one were added to a solution prepared by the addition of 5.01 g of m-methoxy-α-nitrotoluene to 60 ml of 0.05-N methanolic sodium methylate solution and the resulting light-yellow solution was allowed to stand at room temperature under an argon atmosphere. Crystals precipitated. The suspension was cooled to 0° C, filtered under vacuum and the residue was washed with 20 ml of ice-cold methanol and dried at 50° C and 11 Torr for 2 hours to give 6.65 g of colorless crystals melting at 111°-112° C. Recrystallization from 60 ml of isopropyl ether gave 5.3 of pure epimer of 17β-tert.butoxy-3-methoxy-6-nitro-9,10-seco-estra-1,3,5(10)-trien-9-one as colorless prisms melting at 116°-117° C; $[\alpha]_D^{25}$ = +13.8 ($c$ = 1.0 in chloroform); NMR (CDCl$_3$): 1.07 ppm (3H, singlet) C—18—CH$_3$.

The combined filtrates were treated with 0.2 ml of glacial acetic acid and concentrated under a water-jet vacuum on a bath at 40° C. The residue was dissolved in 80 ml of ether and the solution was washed with water, dried over anhydrous sodium sulphate and concentrated under a water-jet vacuum on a bath 40° C. The residue, 6.4 g of a yellow oil, was dissolved in 20 ml of ether and the solution was added to a column (0.06-2 mm) of 640 g of silica gel prepared with 9 parts by volume of n-hexane and 1 part by volume of ether. Elution with a total of 3.5 l. of the same solvent mixture gave, after concentration, 0.4 g of residue which consisted mainly of a dimer of the methylene ketone. By elution with a total of 8 l. of a mixture of 7.5 parts by volume of n-hexane and 2.5 parts by volume of ether, there were obtained, after concentration (finally on a bath at 50° C and 0.01 Torr), 5.0 g of a yellow-colored oil. According to the thin-layer chromatogram and the NMR spectrum, this oil consists of a ca 1:1 mixture of the aforementioned crystalline nitro compound of melting point 116°-117° C and its oily C-6 epimer; NMR (CDCl$_3$): 0.64 ppm (3H, singlet) C—18—CH$_3$.

b. A solution of 4.03 g of (+)-17β-tert.butoxy-3-methoxy-6-nitro-9,10-seco-estra-1,3,5(10)-trien-9-one (crystalline epimer) in 40 ml of dimethlformamide was treated with 4.0 g of 5% palladium/carbon and the system was evacuated and subsequently shaken in a hydrogen atmosphere. After 3 hours, the hydrogen uptake amounted to only 1 ml per minute. After a further hour, the hydrogenation was stopped. The catalyst was filtered under vacuum, washed with 20 ml of methylene chloride and the filtrate was poured on to 400 ml of water. The resulting emulsion was extracted with a total of 150 ml of ether. The ethereal extract was washed first with 20 ml of 0.5-N hydrochloric acid, then with water and dried over anhydrous sodium sulphate. After filtration and concentration, finally at 50° C and 0.01 Torr, there were obtained 3.5 g of an oil. The oil was dissolved in a small amount of benzene and added to a column of 200 g of silica gel prepared in benzene. Elution with a mixture of 49 parts by volume of benzene and 1 part by volume of ethyl acetate initially gave slight amounts of an apolar oil and subsequently 3.2 g of residue which, after distillation in a bulb-tube, yielded 2.9 g of (+)-17β-tert.butoxy-3-methoxy-9,10-seco-estra-1,3,5(10)-trien-9-one as a slightly yellow colored oil of boiling point 190°-200° C/0.01 Torr; $[\alpha]_D^{25}$ = +26.3° ($c$ = 1.01 in chloroform).

EXAMPLE 2

To 20 ml of a 1-N methanolic sodium methylate solution were added dropwise at 0° C with stirring and gassing with argon, firstly 3.34 g of m-methoxy-α-nitrotoluene and then, within 15 minutes, a solution of 5.0 g of (+)-1β-t-butoxy-3aα,6,7,7a-tetrahydro-7aβ-methyl-4-methylene-indan-5(4H)-one in 30 ml of methanol. The cooling bath was removed and the yellowish solution was stirred at room temperature under argon for 4 hours. After this time, all of the methylene ketone had reacted according to thin-layer chromatography. The solution was treated with 1.25 ml of glacial acetic acid and concentrated under a water-jet vacuum on a bath at 40° C. The residue was taken up in 100 ml of ether. The solution was washed with water and dried over anhydrous sodium sulphate. After concentration on a bath at 40° C, finally at 11 Torr, there were obtained 8.7 g of a brownish oil. The oil was dissolved in 15 ml of ether and chromatographed on a column of 350 g of silica gel prepared with 19 parts by volume of n-hexane and 1 part by volume of ether. The column was first eluted with 4 l of the same solvent mixture. The eluate contained m-methoxy-α-nitrotoluene and dimers of (+)-1β-tert.butoxy-3aα, 6, 7,7a-tetrahydro-7aβ-methyl-4-methylene-indan-5(4H)-one. Subsequent elution with 1.5 l. of a mixture consisting of 9 parts by volume of n-hexane and 1 part by volume of ether yielded 2.2 g of the C-6 epimeric mixture of (+)-17β-tert.butoxy-3-methoxy-6-nitro-9, 10-seco-estra-1,3,5(10)-trien-9-one. After crystallization from 10 ml of isopropyl ether, there were obtained 1.2 g of crystals melting at 115°–116° C. Further elution with 1.5 l. of a mixture consisting of 4 parts by volume of n-hexane and 1 part by volume of ether gave a further 1.8 g of the epimer mixture (1:1 according to NMR).

EXAMPLE 3

To a solution of 5.01 g of m-methoxy-α-nitrotoluene in 30 ml of benzene were added with stirring at room temperature firstly 4.22 ml of triethylamine and then 7.32 g of (+)-1β-tert.butoxy-3aα,6,7,7a-tetrahydro-7aβ-methyl-4-methylene-indan-5(4H)-one. The yellowish solution was left under an argon atmosphere at room temperature for 68 hours, after which time the methylene ketone could no longer be detected in the thin-layer chromatogram. The solution was washed with a total of 80 ml of ice-cold 1-N hydrochloric acid, with 30 ml of a 5% sodium bicarbonate solution and water. After drying over anhydrous sodium sulphate and concentration, finally at 50° C and 14 Torr, 14 g of a brown oil were obtained. This was dissolved in 20 ml of ether and added to a column of 420 g of silica gel prepared with n-hexane. Elution with 5.5 l. of a mixture consisting of 19 parts by volume of n-hexane and 1 part by volume of ether gave 3.1 g of an oily residue which consisted essentially of m-methoxy-α-nitrotoluene and dimers of the methylene ketone. Subsequent elution with 5 l. of an n-hexane/ether mixture (9:1) and 5 l. of an n-hexane/ether mixture (4:1) gave, after concentration (finally at 50° C/0.01 Torr), 9.0 g of 17β-tert.butoxy-3-methoxy-6-nitro-9,10-seco-estra-1,3, 5(10)-trien-9-one which, according to the NMR spectrum, consisted of a ca 1:1 mixture of the two C-6 epimers. By crystallization from 50 ml of isopropyl ether/n-hexane (1:1) and recrystallization from isopropyl ether, there could be separated a total of 3.6 g of crystals melting at 115.5°–116.5° C.

EXAMPLE 4

A solution of 7.28 g of m-α-dinitrotoluene in 50 ml of absolute dimethylformamide at 0° C was treated portionwise within 2 minutes with a total of 1.92 g of a 50% sodium hydride suspension in mineral oil. To the red-brown suspension obtained was added dropwise at 0° C within 30 minutes with stirring and gassing with argon a solution of 10.38 g of (+)-1β-tert.butoxy-3aα,6,7,7a-tetrahydro-7aβ-methyl-4-methylene-indan-5(4H)-one in 65 ml of absolute dimethylformamide. The mixture was stirred in an argon atmosphere firstly for 2 hours at 0° C and then for a further 3 hours at 25° C. The solution was poured on to 400 ml of 0.1-N acetic acid at 0° C and the resulting emulsion was extracted three times with 200 ml of ether. The ethereal extracts were washed with 100 ml of 5% sodium bicarbonate solution, twice with 100 ml of water and dried over sodium sulphate. Filtration and concentration of the filtrate under a water-jet vacuum up to 11 Torr on a bath at 40° C gave 18.2 g of a brownish resin. The resin was dissolved in 20 ml of ether and the solution was added to a column of 720 g of silica gel prepared with n-hexane. The column was eluted first with 3 l. of n-hexane. Subsequent elution with 6 l. of a mixture of 9 parts by volume of n-hexane and 1 part by volume of ether as well as 2 l. of a mixture of 85 parts by volume of n-hexane and 15 parts by volume of ether gave, after combination of the eluates and concentration (finally at 50° C and 11 Torr), 1.3 g of a residue which consisted mainly of a dimer of the methylene ketone. By elution with 14 l. of n-hexane/ether (85:15) and concentration, finally at 50° C and 0.01 Torr, there were obtained 14.6 g of 17β-tert.butoxy-3,6-dinitro-9,10-seco-estra-1, 3,5(10)-trien-9-one (C-6 epimeric mixture). By dissolution in 40 ml of isopropyl ether and storage for 16 hours at 0° C, there were obtained 8.0 g of a pure epimer as light yellow colored crystals melting at 105°–106.5° C; $[\alpha]_D^{25} = -11°$ ($c = 1.0$ in chloroform); NMR (CDCl$_3$): 1.05 ppm (3H, singlet) C—18—CH$_3$. The oily residue from the mother liquor consisted of a mixture of the crystalline isomer melting at 105° –106.5° C and its C-8 epimer according to thin-layer chromatography and the NMR spectrum; NMR (CDCl$_3$): 0.85 ppm (3H, singlet) C—18—CH$_3$.

EXAMPLE 5

8.2 g of (+)-1β-tert.butoxy-3aα,6,7,7a-tetrahydro-7aβ-methyl-4-methylene-indan-5(4H)-one were added to a solution of 5.46 g of m-α-dinitrotoluene in 60 ml of 0.05-N methanolic sodium methylate and the yellow-orange solution obtained was allowed to stand for 72 hours at room temperature in an argon atmosphere. The suspension was cooled to 0° C, filtered under vacuum and the residue was washed with 20 ml of ice-cold methanol and dried for 2 hours at 40° C and 11 Torr to give 9.30 g of light yellow crystals melting at 103.5°–105° C. The mother liquor and methanolic washings were combined and concentrated to a volume of 30 ml under a water-jet vacuum on a bath at 40° C. Over a period of 72 hours, an additional 0.86 g of crystals melting at 104°–105.5° C separated from the solution. The mother liquor was treated with 0.2 ml of glacial acetic acid and concentrated under a water-jet vacuum on a bath at 40° C. The residue was taken up in ether and the ethereal solution was washed with water and dried over anhydrous sodium sulphate. The residue, 3.5 g of a brownish foam, remaining after filtration and concentration at 40° C in vacuo up to 11 Torr gave, after chromatography on 175 g of silica gel (0.06-2 mm) and elution with 2 l. of a mixture of 4 parts of n-hexane and 1 part of ether, 0.85 g of dimers of the methylene ketone and, by subsequent elution with 3 l. of the same solvent mixture, 1.52 g of 17β-tert.butoxy-3,6ε-dinitro-9,10-seco-estra-1,3,5(10)-trien-9-one.

EXAMPLE 6

A solution of 3.75 g of 17β-tert.butoxy-3,6ε-dinitro-9,10-seco-estra-1,3,5(10)-trien-9-one in 30 ml of dimethylformamide was treated with 6 g of 5% palladium/carbon and the system was evacuated and subsequently shaken in a hydrogen atmosphere. The hydrogen uptake ceased after 5 hours. The catalyst was filtered under vacuum, washed with 50 ml of methylene chloride and the filtrate was concentrated, finally at 80° C and 0.01 Torr, to give 2.95 g of a brown oil. A sample was purified by preparative thinlayer chromatography on silica gel plates using n-hexane lacetone (3:1) mixture as the eluant. There was obtained 3-amino-17β-tert.butoxy-9,10-seco-estra-1,3,5(10)-trien-9-one as an oil; NMR (CDCl$_3$): 1.0 ppm (3H, singlet) (C—18—CH$_3$.

EXAMPLE 7

A solution of 2.09 g of crystalline 17β-tert. butoxy-3,6-dinitro-9,10-seco-estra-1,3,5(10)-trien-9-one in 20 ml of dimethylformamide was treated with 3 g of 5% palladium/carbon and the system was evacuated and shaken in a hydrogen atmosphere until the hydrogen uptake amounted to only 1 ml per 1 minute (3 hours). The suspension was filtered under vacuum and the residue was washed with 20 ml of methylene chloride and the filtrate diluted with 400 ml of water. The resulting emulsion was extracted with a total of 200 ml of ether. The ethereal solution was washed with water and dried over anhydrous sodium sulphate. The residue (1.75 g) remaining after removal of the solvent on a bath at 40° C and 11 Torr was diluted with 2 ml of pyridine, 2 ml of acetic anhydride were added and the solution was left at room temperature for 1 hour. The mixture was diluted with 50 ml of water and the resulting emulsion extracted with 50 ml of ether. The ethereal solution was washed with 10 ml of 1—N hydrochloric acid, with 20 ml of a saturated sodium bicarbonate solution and finally with water to neutrality. The residue obtained after removal of the ether was chromatographed on 72 g of silica gel. Elution with ether gave firstly 50 mg of apolar fractions and subsequently a total of 1.42 g of 3-acetamino-17β-tert.butoxy-9,10-seco-estra-1,3,5(10)-trien-9-one as an oil; $[\alpha]_D^{585} = +26°$ ($c = 0.1$ in dioxane); NMR (CDCl$_3$): 1.02 ppm (3H, singlet) C—18—CH$_3$. By subsequent elution with a 1:1 mixture of methylene chloride and ether, containing 2% methanol, there were obtained 0.278 g of crystalline product. Recrystallization from methylene chloride/isopropyl ether gave 0.187 g of a homogeneous epimer of 3,6-bis-(acetamino)-17β-tert.-butoxy-9,10-seco-estra-1,3,5(10)-triene melting at 248.5°–250.5° C; $[\alpha]_D^{25} = -24°$ ($c = 0.1$ in dioxane).

EXAMPLE 8

A solution of 16.7 g of m-methoxy-α-nitrotoluene in 400 ml of dimethylformamide was treated with 0.5 g of sodium methylate and 26.9 g of (+)-1β-tert.butoxy-3aα,6,7,7a-tetrahydro-7aβ-methyl-4-methylene-indan-5(4H)-one and the mixture was allowed to stand for 16 hours at room temperature. The yellow solution was treated with 0.6 ml of glacial acetic acid and 40 g of 10% palladium/carbon and then shaken in a hydrogen atmosphere. The hydrogen uptake (9.7 l.) was complete after 5 hours. The suspension was filtered under suction. The residue was washed with 50 ml of dimethylformamide and 30 ml of methylene chloride and the filtrate oured into 4 l. of water. The emulsion was extracted with a total of 3 l. of ether and the ethereal solution was washed with a total of 3 l. of water and concentrated on a bath at 50° C. There was obtained crude (+)-17β-tert.butoxy-3-methoxy-9,10-seco-estra-1,3,5(10)-trien-9-one.

EXAMPLE 9

(a) A suspension of 4.86 g of m-benzyloxy-α-nitrotoluene in 40 ml of methanol was treated with 0.1 g of sodium methylate and 4.73 g of (+)-1β-tert.butoxy-3aα,6,7,7a-tetrahydro-7aβ-methyl-4-methylene-indan-5(4H)-one and the solution which formed after stirring for 30 minutes was allowed to stand for 72 hours at room temperature. The mixing consisting of two oily phases was treated with 1 ml of glacial acetic acid and concentrated in a water-jet vacuum on a bath at 40° C.

The residue was taken up in 100 ml of ether. The solution was washed with 100 ml of water, dried over anhydrous sodium sulphate and, after filtration, concentrated in a water-jet vacuum on a bath at 40° C. The residue, 10.1 g of a yellow oil, was chromatographed on a column of 500 g of silica gel prepared with n-hexane/ether (19:1). Elution with 6 l. of the same solvent mixture gave, after concentration, 1.5 g of a residue from which, after treatment with n-hexane, 0.6 g of m-benzyloxy-α-nitrotoluene of melting point 55°–56° C was isolated. Dimers of the methylene ketone were present in the mother liquor. Elution with an additional 2 l. of n-hexane/ether (19:1) gave, after concentration, 1.8 g of a residue. Two crystallizations of the residue from hexane gave 1.1 g of homogeneous epimer of 3-benzyloxy-17β-tert.butoxy-6-nitro-9,10-seco-estra-1,3,5(10)-trien-9-one melting at 97.5°–99.5° C; $[\alpha]_D^{25} = +9.4°$ ($c = 1.0$ in chloroform; NMR (CDCl$_3$): δ 1.02 ppm (3H, singlet) C—18—CH$_3$. Elution with 6 l. of n-hexane/ether (19:1) and with 4 l. of hexane/ether (9:1) yielded, after concentration, 6.2 g of a residue. Recrystallization of the residue from hexane gave 5.6 g of a crystalline product melting at 86°–98° C which, according to thin-layer chromatography and NMR spectroscopy, consisted of a mixture of the aforementioned nitro compound melting at 97.5°–99.5° C and the C-6 epimer; NMR (CDCl$_3$): δ 0.80 ppm (3H, singlet) C—18—CH$_3$.

b. A solution of 6.05 g of C-6 epimeric mixture of 3-benzyloxy-17β-tert.butoxy-6-nitro-9,10-seco-estra-1,3,5(10)-trien-9-one in 50 ml of dimethylformamide was treated with 9 g of 10% palladium/carbon and the system was evacuated and subsequently shaken in a hydrogen atmosphere. 1.8 g of hydrogen were taken up within 5 hours. The catalyst was filtered under suction. The filtrate was added to 0.5 l. of water and the emulsion was extracted with a total of 0.5 l. of ether. The ethereal solution was washed with water, dried over anhydrous sodium sulphate and, after filtration, concentrated in a water-jet vacuum on a bath at 40° C up to 11 Torr. The crystalline residue (3.9 g) gave, after crystallization from methylene chloride/isopropyl ether, 2.7 g of (+)-17β-tert.butoxy-3-hydroxy-9,10-seco-estra-1,3,5(10)-trien-9-one melting at 187°–188° C; $[\alpha]_D^{25} = +28.6°$ ($c = 1.0$ in chloroform).

EXAMPLE 10 a. A solution of 1.97 g of 3,5-dimethoxy-α-nitrotoluene in 20 ml of methanol was treated with 60 mg of sodium methylate and subsequently added to 2.6 g of (+)-1β-tert.butoxy-3aα,6,7,7a-tetrahydro-7aβ-methyl-4-methylene-indan-5(4H)-one. The mixture was stirred for 30 minutes and the solution was allowed to stand for 72 hours at room temperature. After the addition of 0.1 ml of glacial acetic acid, the solution was concentrated in a water-jet vacuum on a bath at 40° C. The residue was taken up in 60 ml of ether and washed with a total of 100 ml of water. After drying over anhydrous sodium sulphate, filtration and concentration in a water-jet vacuum on a bath at 40° C up to 11 Torr, there were obtained 4.7 g of a yellow oil. This oil was chromatographed on a column of 250 g of silica gel prepared with n-hexane/ether (19:1). Elution with 6.5 l. of the same solvent mixture gave, after concentration, 0.9 g of a residue consisting of dimers of the methylene ketone and 3,5-dimethoxy-α-nitrotoluene. Elution with an additional 2.5 l. of the foregoing solvent mixture yielded 1.2 g of a residue. Two crystallizations of this residue from pentane gave 0.75 g of a homogeneous epimer of 17β-tert.butoxy-1,3-dimethoxy-6-nitro-9,10-seco-estra-1,3,5(10)-trien-9-one melting at 90.5°–91° C; $[\alpha]_D^{25} = +34.7°$ ($c = 1.0$ in methanol); NMR (CDCl$_3$): δ 1.03 ppm (3H, singlet) C—18—CH$_3$. Elution with 6 l. of hexane/ether (9:1) gave, after concentration, 2.2 g of an oily residue which, according to NMR spectroscopy, consisted of a mixture of the foregoing nitro compound melting at 90.5°–91° C and the C-6 epimer; NMR (CDCl$_3$): δ 0.85 ppm (3H, singlet) C—18—CH$_3$.

b. The 17β-tert.butoxy-1,3-dimethoxy-6-nitro-9,10-seco-estra-1,3,5(10)-trien-9-one obtained according to paragraph (a) was hydrogenated to give 17β-tert.butoxy-1,3-dimethoxy-9,10-seco-estra-1,3,5(10)-trien-9-one by the method described in paragraph (b) of Example 9.

EXAMPLE 11 a. A solution of 3.34 g of m-methoxy-α-nitrotoluene in 40 ml of methanol was treated with 0.1 g of sodium methylate and 5 g of (+)-1β-tert.butoxy-3aα,6,7,7a-tetrahydro-7aβ-ethyl-4-methyleneindan-5(4H)-one and allowed to stand for 72 hours at room temperature. After the addition of 1 ml of glacial acetic acid, the yellow solution was concentrated in a water-jet vacuum on a bath at 40° C. The residue was taken up in 150 ml of ether and the solution was washed with 100 ml of water and then dried over anhydrous sodium sulphate. The residue, 8.5 g of a yellow resin, remaining after concentration (finally at 40° C and 11 Torr), was chromatographed on a column of 2 kg of silica gel prepared with hexane/ether (9:1). Elution with the same solvent mixture gave a mixture of m-methoxy-α-nitrotoluene and dimers of the methylene ketone and then 6.81 g of the C-6 epimer mixture of 17β-tert.-butoxy-3-methoxy-18-methyl-6-nitro-9,10-seco-estra-1,3,5(10)-trien-9-one. Two crystallizations from methanol at −20° C yielded 3.55 g of a homogeneous epimer melting at 113°–114° C; $[\alpha]_D^{25} = +30°$ ($c = 1.034$ in dioxane).

b. A solution of 1.3 g of the 6 epimeric C- mixture of 17β-tert.-butoxy-3-methoxy-18-methyl-6-nitro-9,10-seco-estra-1,3,5(10)-trien-9-one in 12 ml of dimethylformamide was treated with 1.25 g of 5% palladium/carbon. The system was evacuated and shaken in a hydrogen atmosphere. 0.31 l. of hydrogen was taken up within 3 hours. The catalyst was filtered under suction. The filtrate was treated with 130 ml of water and the emulsion extracted with a total of 150 ml of ether. The ethereal solution was washed with water, dried over anhydrous sodium sulphate and, after filtration, concentrated in a water-jet vacuum on a bath at 40° C. The residue was chromatographed on a column of 30 g of silica gel in ether. Elution with 400 ml of ether gave, after concentration and drying for 30 minutes at 40° C and 0.01 Torr, 1.0 g of (+)-17β-tert.butoxy-3-methoxy-18-methyl-9,10-seco-estra-1,3,5(10)-trien-9-one as an oil; $[\alpha]_D^{25} = +13°$ ($c = 0.102$ in dioxane).

EXAMPLE 12 a. A suspension of 2.43 g of m-benzyloxy-α-nitrotoluene in 20 ml of methanol was treated with 54 mg of sodium methylate and 2.5 g of (+)-1β-tert.butoxy-3aα,6,7,7a-tetrahydro-7aβ-ethyl-4-methylene-indan-5(4H)-one and the solution obtained after stirring for 10 minutes was allowed to stand for 72 hours at room temperature. After treatment with 0.1 ml of glacial acetic acid, the suspension was concentrated in a water-jet vacuum on a bath at 40° C. The solid residue obtained was taken up in 100 ml of ether and the solution washed with 150 ml of water and dried over anhydrous sodium sulphate. The residue (5.08 g) remaining after concentration (finally at 40° C and 11 Torr), gave, from methanol, 3.5 g of the crystalline C-6 epimeric mixture of 3-benzyloxy-17β-tert.butoxy-18-methyl-6-nitro-9,10-seco-estra-1,3,5(10)-trien-9-one. Three crystallizations from acetone/hexane gave a pure epimer; melting point 134°–135° C; $[\alpha]_D^{25} = -1.2°$ ($c = 0.996$ in chloroform).

b. The 3-benzyloxy-17β-tert.butoxy-18-methyl-6-nitro-9,10-seco-estra-1,3,5(10)-trien-9-one obtained according to paragraph (a) was hydrogenated to give 17β-tert.butoxy-3-hydroxy-18-methyl-9,10-seco-estra-1,3,5(10)-trien-9-one by the method described in paragraph (b) of Example 9.

EXAMPLE 13 a. A solution of 0.99 g of 3,5-dimethoxy-α-nitrotoluene in 10 ml of methanol was treated with 30 mg of sodium methylate and 1.25 g of (+)-1β-tert.butoxy-3aα,6,7,7a-tetrahydro-7aβ-ethyl-4-methylene-indan-5(4H)-one and the mixture was stirred at room temperature for 88 hours. After treatment with 0.1 ml of glacial acetic acid, the mixture was concentrated in a water-jet vacuum on a bath at 40° C, the residue was taken up in 50 ml of ether and the solution washed with a total of 100 ml of water. After drying over anhydrous sodium sulphate, filtration and concentration (finally at 40° C and 11 Torr), there were obtained 2.3 g of an oil. The oil was chromatographed on a column of 450 g of silica gel prepared with hexane/ether (14:1). Elution with the same solvent mixture gave 1.76 g of the C-6 epimeric mixture of 17β-tert.butoxy-1,3-dimethoxy-18-methyl-6-nitro-9,10-seco-estra-1,3,5(10)-trien-9-one as a resin; $[\alpha]_D^{25} = +9°$ ($c = 0.1$ in dioxane).

b. The 17β-tert.butoxy-1,3-dimethoxy-18-methyl-6-nitro-9,10-seco-estra-1,3,5(10)-trien-9-one obtained according to paragraph (a) was hydrogenated to give 17β-tert.butoxy-1,3-dimethoxy-18-methyl-9,10-seco-estra-1,3,5(10)-trien-9-one by the method described in paragraph (b) of Example 9.

EXAMPLE 14 a. A suspension of 0.73 g of m-α-dinitrotoluene in 8 ml of methanol was treated with 22 mg of sodium methylate and 1 g of (+)-1β-tert.butoxy-3aα,6,7,7a-tetrahydro-7aβ-ethyl-4-methylene-indan-5(4H)-one and the solution formed after stirring for 30 minutes was allowed to stand for 72 hours at room temperature. The suspension was filtered under suction after cooling to −5° C. The residue, after crystallization from isopropyl ether, yielded 0.62 g of a homogeneous epimer of 17β-tert.butoxy-3,6-dinitro-18-methyl-9,10-seco-estra-1,3,5(10)-trien-9-one melting at 108°–109° C; $[\alpha]_D^{25} = +4°$ ($c = 0.1$ in dioxane). The mother liquors were combined, treated with 0.1 ml of glacial acetic acid and concentrated in a water-jet vacuum on a bath at 40° C. The residue was chromatographed on a column of 200 g of silica gel prepared with hexane/ether (14:1). Elution with the same solvent mixture gave, after concentration, 0.55 g of nitro adduct in the form of the C-6 epimeric mixture.

b. A suspension prepared from 0.98 g of (+)-17β-tert.butoxy-3,6-dinitro-18-methyl-9,10-seco-estra-1,3,5(10)-trien-9-one, 1.5 g of 5% palladium/carbon and 7.5 ml of dimethylformamide was shaken at room temperature in a hydrogen atmosphere. After completion of the hydrogen uptake (0.395 l. in 3.5 hours), the catalyst was filtered under suction and the filtrate concentrated on a bath at 50° C at 0.01 Torr. The residue, which solidified upon cooling, gave after recrystallization from ether/pentane and then from methanol, 0.4 g of (+)-3-amino-17β-tert.butoxy-18-methyl-9,10-seco-estra-1,3,5(10)-trien-9-one melting at 119°–120° C; $[\alpha]_D^{25} = +12°$ ($c = 0.98$ in chloroform).

EXAMPLE 15

A solution of 1.56 g (+)-17β-tert.butoxy-3-methoxy-9,10-seco-estra-1,3,5(10)-trien-9-one was treated over a period of 3 minutes with 30 ml of 10-N hydrochloric acid with vigorous stirring under nitrogen. The mixture was stirred for 3 hours at room temperature for 30 minutes with ice-cooling and was then filtered. The precipitate was washed three times with 15 ml-portions of water and dried under reduced pressure to give (+)-17β-tert.-butoxy-3-methoxy-estra-1,3,5(10)-9(11)-tetraene melting at 133°–134° C (from methanol).

EXAMPLE 16

0.679 g of (+)-17β-tert.butoxy-3-methoxy-estra-1,3,5(10)-9(11)-tetraene was hydrogenated at atmospheric pressure in 25 ml of ethyl acetate in the presence of 0.2 g of pre-equilibrated 5% palladium/carbon catalyst. After stirring for 1.5 hours, 50 ml of hydrogen was absorbed. The catalyst was filtered and washed with ethyl acetate. Evaporation gave 17β-tert.butoxy-3-methoxy-estra-1,3,5(10)-trien as a light-yellow oil melting at 91°–92.5° C.

We claim:

1. A compound of the formula

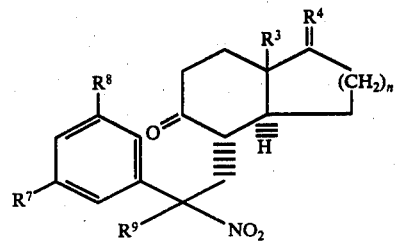

wherein $R^3$ is lower alkyl; $R^4$ is

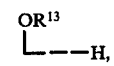

wherein $R^{13}$ is lower alkyl; $R^7$ and $R^8$ are each independently hydrogen, benzyloxy, diphenylmethoxy, triphenylmethoxy or $OR^5$ wherein $R^5$ is lower alkyl; $R^9$ is hydrogen; and $n$ is 1 or 2.

2. The compound of claim 1 wherein $R^3$ is methyl or ethyl; $R^4$ is tert.-butoxy or methoxymethylene and $n$ is 1.

3. The compound according to claim 2 which is 17β-tert.-butoxy-3-methoxy-6-nitro-9,10-seco-estra-1,3,5(10)-trien-9-one.

4. The compound according to claim 2 which is 3-benzyloxy-17β-tert.-butoxy-6-nitro-9,10-seco-estra-1,3,5(10)-trien-9-one.

5. The compound according to claim 2 which is 17β-tert.-butoxy-1,3-dimethoxy-6-nitro-9,10-seco-estra-1,3,5(10)-trien-9-one.

6. The compound according to claim 2 which is 17β-tert.butoxy-3-methoxy-18-methyl-6-nitro-9,10-seco-estra-1,3,5(10)-trien-9-one.

7. The compound according to claim 2 which is 3-benzyloxy-17β-tert.-butoxy-18-methyl-9,10-seco-estra-1,3,5(10)-trien-9-one.

8. The compound according to claim 2 which is 17β-tert.butoxy-1,3-dimethoxy-18-methyl-6-nitro-9,10-seco-estra-1,3,5(10)-trien-9-one.

9. The compound 17β-tert.-butoxy-3,6-dinitro-9,10-seco-estra-1,3,5(10)-trien-9-one.

10. The compound 17β-tert.-butoxy-3,6-dinitro-18-methyl-9,10-seco-estra-1,3,5(10)-trien-9-one.

* * * * *